US010149739B2

(12) United States Patent
Bernstein (10) Patent No.: US 10,149,739 B2
(45) Date of Patent: Dec. 11, 2018

(54) ORTHODONTIC BRACKET FOR PRIMARY TEETH (71) Applicant: Rael Bernstein, Santa Rosa, CA (US)

(72) Inventor: Rael Bernstein, Santa Rosa, CA (US)

(*) Notice: Subject to any disclaimer, the term of this patent is extended or adjusted under 35 U.S.C. 154(b) by 6 days.

(21) Appl. No.: 15/057,751

(22) Filed: Mar. 1, 2016

(65) Prior Publication Data
US 2016/0287356 A1 Oct. 6, 2016

Related U.S. Application Data (60) Provisional application No. 62/140,419, filed on Mar. 30, 2015, provisional application No. 62/161,261, filed on May 14, 2015.

(51) Int. Cl.
A61C 3/00 (2006.01)
A61C 7/28 (2006.01)
A61C 7/18 (2006.01)

(52) U.S. Cl.
CPC ............... *A61C 7/282* (2013.01); *A61C 7/18* (2013.01)

(58) Field of Classification Search
CPC ........... A61C 7/28; A61C 7/228; A61C 7/282; A61C 7/18
USPC .................................................. 433/8, 10, 17
See application file for complete search history.

(56) References Cited

U.S. PATENT DOCUMENTS

| | | | | |
|---|---|---|---|---|
| 4,196,517 A * | 4/1980 | Forster | ................... | A61C 7/285 433/17 |
| 4,322,206 A * | 3/1982 | Reynolds | ............... | A61C 7/282 433/17 |
| 4,781,582 A * | 11/1988 | Kesling | .................. | A61C 7/282 433/17 |
| 4,927,362 A * | 5/1990 | Snead | .................... | A61C 7/282 433/17 |
| 4,948,367 A * | 8/1990 | Haas | ...................... | A61C 7/282 433/24 |
| 5,288,229 A * | 2/1994 | Huff | ...................... | A61C 7/282 433/17 |
| 5,556,277 A * | 9/1996 | Yawata | ................. | A61C 7/143 433/17 |
| 5,707,232 A * | 1/1998 | Strauss | ................. | A61C 7/282 433/17 |
| 5,727,941 A * | 3/1998 | Kesling | ................. | A61C 7/282 433/17 |

(Continued)

OTHER PUBLICATIONS

International Search Report and Written Opinion dated Jul. 6, 2016, 11 pages.

*Primary Examiner* — Nicholas Lucchesi
(74) *Attorney, Agent, or Firm* — Waller Lansden Dortch & Davis LLP; Blake M. Bernard (57) ABSTRACT

An orthodontic bracket for receiving an arch wire of orthodontic patients having both primary teeth and permanent teeth, the orthodontic bracket including a pad sized to fit on one of the primary teeth, the pad extending a first distance generally in a longitudinal direction and a second distance generally in a lateral direction, the first distance being greater than the second distance. An eyelet can extend from the pad, the eyelet including an aperture defined through the eyelet, the aperture having a central axis oriented transverse to the lateral direction. The aperture can slidingly receive the arch wire. A method including bonding the pad of the orthodontic bracket to one of the primary teeth of the patient.

6 Claims, 5 Drawing Sheets

(56) References Cited

U.S. PATENT DOCUMENTS

| | | | | |
|---|---|---|---|---|
| 6,126,441 | A * | 10/2000 | Tenti | A61C 7/282 433/17 |
| 6,428,314 | B1 * | 8/2002 | Jones, Jr. | A61C 7/282 433/17 |
| 6,932,598 | B1 * | 8/2005 | Anderson | A61C 7/36 433/18 |
| 8,157,562 | B2 * | 4/2012 | Swain | A61C 7/143 433/9 |
| 2003/0064343 | A1 * | 4/2003 | Devanathan | A61C 7/16 433/9 |
| 2003/0170585 | A1 * | 9/2003 | Wilkerson | A61C 7/282 433/17 |
| 2004/0121278 | A1 | 6/2004 | Kelly et al. | |
| 2008/0113310 | A1 | 5/2008 | Andreiko | |
| 2010/0092903 | A1 | 4/2010 | Sabilla | |
| 2011/0212408 | A1 * | 9/2011 | Kalange | A61C 7/282 433/17 |
| 2012/0202163 | A1 | 8/2012 | Vashi | |
| 2013/0252195 | A1 * | 9/2013 | Popat | A61C 7/10 433/24 |
| 2014/0356800 | A1 * | 12/2014 | Ariza | A61C 7/282 433/17 |
| 2015/0111166 | A1 * | 4/2015 | Ariza | A61C 7/282 433/9 |
| 2015/0125803 | A1 * | 5/2015 | Ariza | A61C 7/14 433/9 |

* cited by examiner

ORTHODONTIC BRACKET FOR PRIMARY TEETH

CROSS-REFERENCES TO RELATED APPLICATIONS

This application is a non-provisional of U.S. Provisional Patent Application Ser. No. 62/140,419 filed Mar. 30, 2015 entitled Orthodontic Bracket and U.S. Provisional Patent Application Ser. No. 62/161,261 filed May 15, 2015 entitled Orthodontic Bracket For Primary Teeth, both of which are herein incorporated by reference in their entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to orthodontic brackets for primary teeth for patients having a combination of permanent teeth and primary teeth.

More particularly, the present disclosure relates to an orthodontic bracket for primary teeth, the orthodontic bracket being used for Phase 1 or mixed dentition interceptive treatment where patients have a mixture of primary teeth as well as permanent teeth. For many orthodontic patients, it is often necessary or desired to apply an outward force or pressure from the palatal or lingual (tongue) side of the teeth toward the facial (lip) side of the teeth in order to achieve arch width development, or to help spread the teeth outward. For instance, such outward force can be used to correct cross bites, alleviate crowding and/or other conditions where it is desirable to create or increase arch width of the top teeth, the bottom teeth, or both.

One conventional method of increasing arch width is the use of lingual expansion appliances such as a rapid palatal expander, a quadhelix system, or removable expanders. These expansion devices are located on the palatal or lingual side of the teeth. As such, these appliances can be uncomfortable for the patient as the tongue space is encroached. Having a lingual expansion appliance in the tongue space can also make speech difficult. Another problem with lingual expansion appliances is that food can become stuck between the appliances and the roof or floor of the mouth and be difficult to remove, which can potentially cause infection inside the mouth and foul odors. These appliances also typically apply a large force to the teeth so that arch development can be developed more quickly, which can be painful for the patient.

In order to help overcome the problems with lingual expansion appliances, orthodontists have begun using passive self-ligating techniques to develop arch width in patients. Passive self-ligating systems include a biased arch wire that can be used to bias or apply a gentle outward force to the teeth of a patient to develop arch width more gradually. Brackets used for passive self-ligating systems include (1) a channel for the arch wire to be received in, and (2) a movable cover to selectively enclose the arch wire. The bracket is configured such that the bracket and the tooth are movable along the arch wire, thereby allowing the teeth to gradually expand and adjust freely as the arch wire applies an outward force to the teeth. Unlike traditional braces that are bound to the wire with an elastomeric tie that creates friction on the wire, passive self-ligating brackets allow relative movement between the wire and the bracket in a reduced friction environment. Passive self-ligating techniques can provide increased comfort compared to lingual expansion appliances as all brackets in such a system can be positioned on the facial side of the teeth.

One problem associated with arch width development in Phase 1 or mixed dentition patients is that traditional brackets and passive self-ligating brackets that can potentially be placed on primary teeth typically include edgewise or rectangular channels that generally conform to the shape of a rectangular arch wire. As such, if traditional or passive-self-ligating brackets are placed on primary teeth, the rectangular channels can cause the traditional brackets to produce torque forces on the primary teeth when larger, rectangular wires that are used to expand the teeth outward twist and turn within the rectangular channels. The twisting of the large rectangular wires can potentially twist and apply a torque force on the teeth via the bracket, which can cause the primary teeth to prematurely become loose and exfoliate early, which is undesirable.

Additionally, traditional brackets and passive self-ligating brackets are designed for permanent teeth, and therefore can be larger than the facial surface of the primary teeth, which can affect the quality of the bond between the bracket and the primary teeth. Larger brackets can also affect cleanliness and hygiene of the teeth as the larger brackets encroach on a patient's gums, which can make the gum line difficult to clean, increasing the risk of gum disease.

Another problem associated with the use of traditional and passive self-ligating brackets on primary teeth is that they are relatively expensive. Primary teeth tend to fall out over time, and if an expensive bracket is placed on the primary teeth, that bracket can simply be thrown away once the primary teeth fall out, which can unnecessarily increase the cost of the treatment. Additionally, in many early treatment protocols, brackets for primary teeth are often removed after a few appointments as the brackets are temporary to support initial wires. As such, because brackets for primary teeth can be disposed of after a relatively short time, the use of more expensive passive self-ligating brackets can be an unnecessary expense.

Because of the problems associated with the use of traditional and passive self-ligating brackets on primary teeth, orthodontics have developed what is called the "2x4 method", where for Phase 1 or mixed dentition patients, brackets are placed on the front 4 and 2 back permanent teeth, while no brackets are placed on the primary teeth. As such, the arch wire bypasses the primary teeth completely. Because the arch wire in such systems extends a significant distance without a supporting bracket, the arch wire can easily be bent or broken; for instance, when a patient chews on a hard food. Broken or bent arch wires can adversely affect the arch development of the patient and oftentimes when the arch wire is bent or broken an emergency visit is required. Broken or bent arch wires can also potentially cut or rip into a patient's cheek, gums, or lips, causing serious pain and discomfort.

What is needed then are improvements to orthodontic brackets for primary teeth.

BRIEF SUMMARY

This Brief Summary is provided to introduce a selection of concepts in a simplified form that are further described below in the Detailed Description. This Summary is not intended to identify key features or essential features of the claimed subject matter.

One aspect of the disclosure is an orthodontic bracket for receiving an arch wire of orthodontic patients having both primary teeth and permanent teeth, the bracket including a pad sized to fit on one of the primary teeth, the pad extending a first distance generally in a longitudinal direction and a second distance generally in a lateral direction, the first distance being greater than the second distance. An eyelet can extend from the pad, the eyelet including an aperture defined through the eyelet, the aperture having a central axis oriented transverse to the lateral direction, the aperture sized to slidingly receive the arch wire. In some embodiments, each of the primary teeth can have a facial surface, and the pad can be sized to fit on the facial surface of one of the primary teeth. In still other embodiments, the aperture can be round.

Such a bracket can help provide a cost-efficient bracket that can be placed on primary teeth for arch width development, and particularly for passive self-ligating bracket systems. The aperture sized to slidingly receive the arch wire can help reduce undesirable torque and friction forces on the primary teeth, which can produce premature dislodging of the primary teeth. The pad sized to fit on one of the patient's primary teeth can help produce a better and more consistent bond between the pad and the primary teeth and help provide improved hygiene with less encroachment on the gum tissue.

Another aspect of the present invention is a method of attaching orthodontic brackets to patients having both primary teeth and permanent teeth for a passive self-ligating braces system, the method including the steps of (a) providing an orthodontic bracket having a pad extending a first distance generally in a longitudinal direction and a second distance generally in a lateral direction, the first distance being greater than the second distance, and an eyelet extending from the pad, the eyelet including a round aperture having a central axis oriented transverse to the lateral direction; and (b) bonding the pad of the orthodontic bracket to one of the primary teeth. In some embodiments, a plurality of similar orthodontic brackets can be provided, and each orthodontic bracket can be bonded to a corresponding primary tooth. As such, all primary teeth of the patient can include an orthodontic bracket of the present disclosure.

One objective of the present disclosure is to provide a cost-efficient bracket for primary teeth which can receive and support an arch wire of an orthodontic patient.

Another objective of the present disclosure is to help reduce the torque forces applied to primary teeth by an edgewise or rectangular arch wire of an orthodontic patient.

Another objective of the present disclosure is to provide a bracket for primary teeth that can be more easily and more comfortably removed during or after treatment.

Another objective of the present disclosure is to help prevent the premature dislodging of primary teeth.

Another objective of the present disclosure is to help provide support to an arch wire between the front and back permanent teeth of a patient.

Numerous other objects, advantages and features of the present disclosure will be readily apparent to those of skill in the art upon a review of the following drawings and description of a preferred embodiment.

DETAILED DESCRIPTION

While the making and using of various embodiments of the present invention are discussed in detail below, it should be appreciated that the present invention provides many applicable inventive concepts that are embodied in a wide variety of specific contexts. The patentable scope of the invention is defined by the claims, and may include other examples that occur to those skilled in the art. The specific embodiments discussed herein are merely illustrative of specific ways to make and use the invention and do not limit the scope of the invention. Those of ordinary skill in the art will recognize numerous equivalents to the specific apparatus and methods described herein. Such equivalents are considered to be within the scope of this invention and are covered by the claims.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

In the drawings, not all reference numbers are included in each drawing, for the sake of clarity. In addition, positional terms such as "upper," "lower," "side," "top," "bottom," "horizontal," "vertical," etc. refer to the apparatus when in the orientation shown in the drawing. A person of skill in the art will recognize that the apparatus can assume different orientations when in use.

Figure 1:
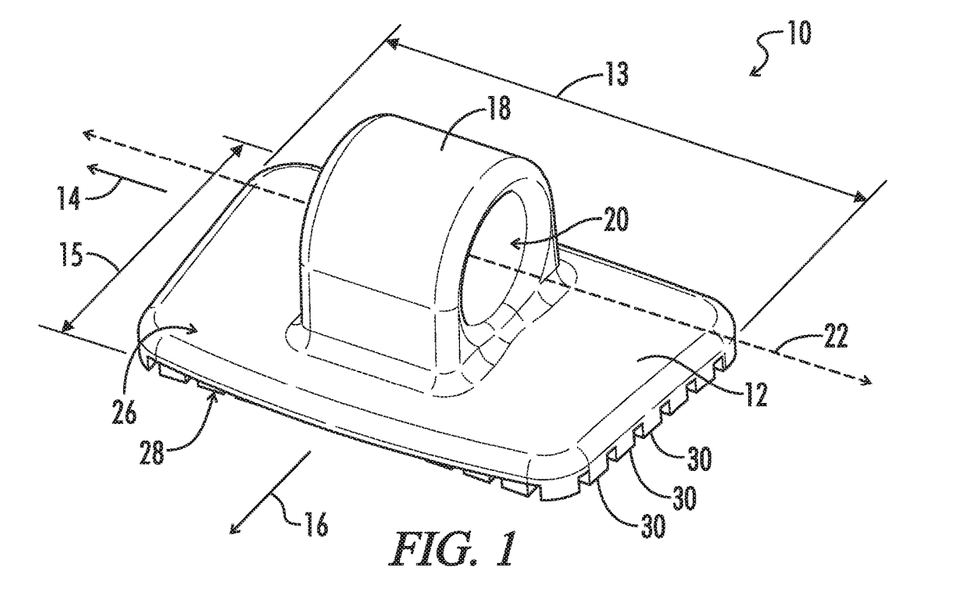
FIG. 1 is a perspective view of an embodiment of an orthodontic bracket of the present disclosure.
Figure 8:
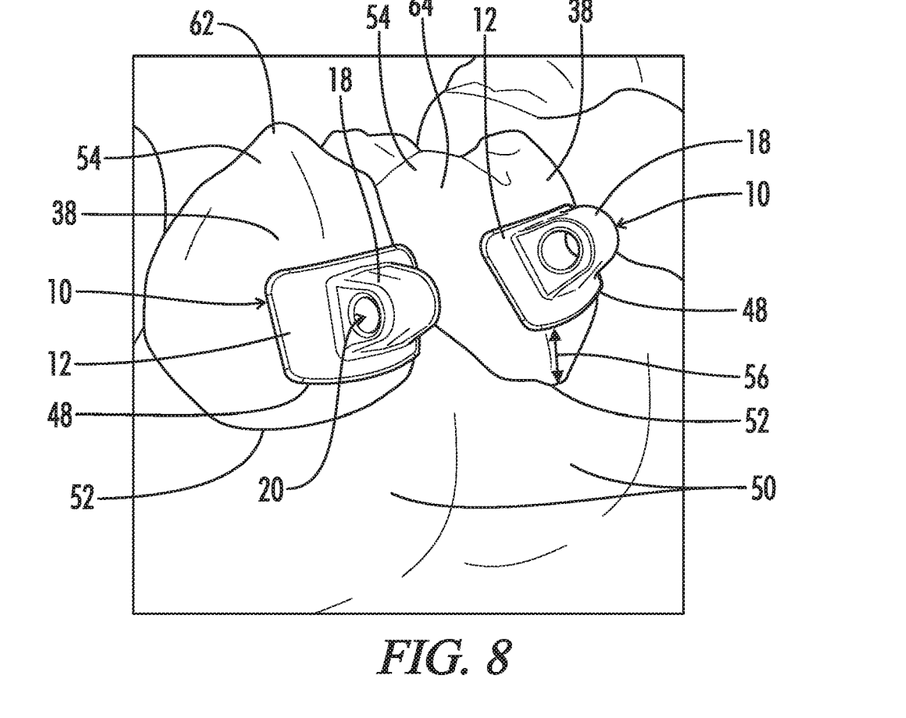
FIG. 8 is a detailed view of the primary teeth shown in FIG. 7

An embodiment of an orthodontic bracket 10 for receiving an arch wire of orthodontic patients having both primary teeth and permanent teeth is shown in FIG. 1. Orthodontic bracket 10 can have a pad 12 which can be sized to fit one of the primary teeth of a patient. As can be seen in FIG. 8, each of a patient's primary teeth 54 can have a facial surface 38. In some embodiments, pad 12 can be sized to fit on and/or within the facial surface 38 of one of primary teeth 54. Facial surface 38 of one of primary teeth 54 can be defined as the surface of the tooth facing a patient's lips or cheeks. Facial surface 38 can also be described as a buccal or labial surface of primary tooth 54. Buccal surfaces are generally located on the back teeth of a patient and face the cheek, while labial surfaces are generally located on the front teeth of the patient and face the lips. In some embodiments, pad 12 can be specifically designed or sized to fit on the C, D, & E teeth of a patient, or the canine teeth and first and second molars of the patient. In some embodiments, pad 12 can be sized such that when pad 12 is placed on a primary tooth, pad 12 is contained within the facial surface of the primary tooth.

Referring again to FIG. 1, pad 12 can extend a first distance 13 generally in a longitudinal direction 14 and a second distance 15 generally in a lateral direction 16, first distance 13 being greater than second distance 15. In some embodiments, the ratio of first distance 13 to second distance 15 can be greater than 1. In other embodiments, the ratio of first distance 13 to second distance 15 can be greater than 1.5. In still other embodiments, the ratio of first distance 13 to second distance 15 can be greater than 2. Bracket 10 can also include an eyelet 18 which extends from pad 12. In some embodiments, when bracket 10 is bonded to a primary tooth, longitudinal direction 14 can be oriented in a substantially horizontal direction, and lateral direction 16 can be oriented in a substantially vertical direction. As such, when bracket 10 is bonded to a primary tooth, first distance 13 can correspond to the width of pad 12 on the primary tooth, and second distance 15 can correspond to the height of pad 12 on the primary tooth. Pad 12 having a larger width than a height when bonded to a primary tooth can help pad 12 better contour and produce a better bond to a primary tooth, which generally has a short and wide facial surface.

Referring again to FIG. 1, eyelet 18 can include an aperture 20 defined through eyelet 18. Aperture 20 can include a central axis 22 which can be oriented transverse to lateral direction 16. In some embodiments, central axis 22 can also be described as being oriented substantially parallel to longitudinal direction 14. In some embodiments, when bracket 10 is positioned on a primary tooth, central axis 22 can be oriented in a substantially horizontal direction. Aperture 20 can be sized to slidingly receive an arch wire 24, shown in FIG. 2. In some embodiments, eyelet 18 can have a rounded distal end extending away from pad 12. As such, when bracket 10 is positioned on a patient's tooth, the rounded distal end of eyelet 18 can help reduce discomfort of the bracket against the patient's lips.

Figure 2:
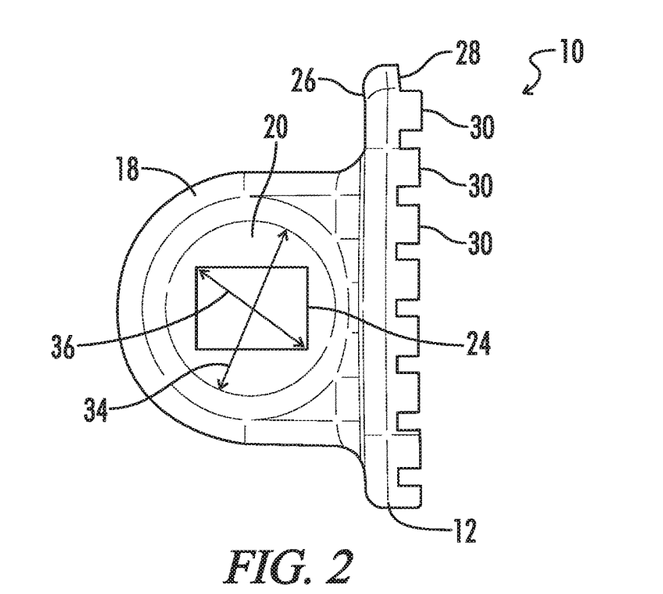
FIG. 2 is a side view of the orthodontic bracket of FIG. 1.
Figure 4:
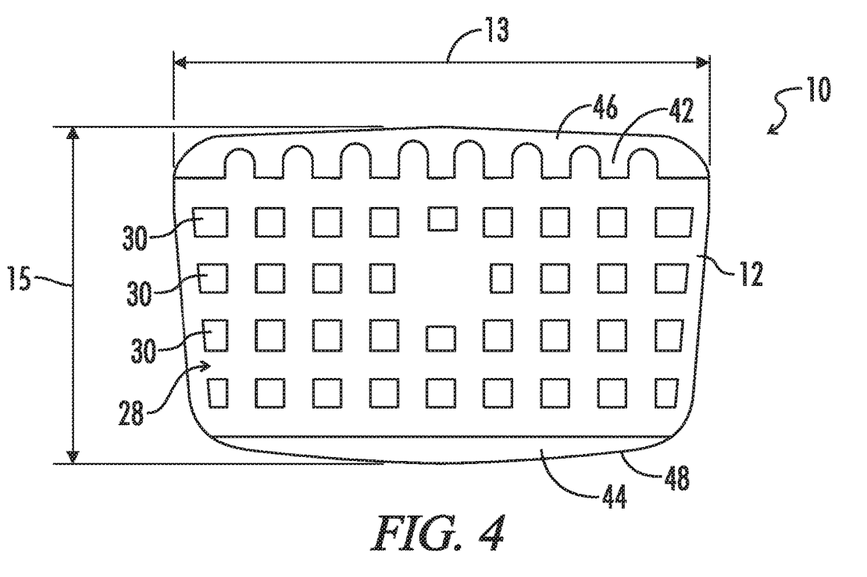
FIG. 4 is a bottom view of the orthodontic bracket of FIG. 1.

As shown in FIG. 2, pad 12 can include a first side 26 and a second side 28. Eyelet 18 can extend from first side 26 of pad 12. In some embodiments, pad 12 can include a plurality of posts 30 extending from second side 28 of pad 12. Posts 30 can extend in a direction away from eyelet 18 and toward a primary tooth to which bracket 10 is bonded. Posts 30 can produce a textured or varying surface on second side 28 of pad 12. When bracket 10 is used in an orthodontics system, second side 28 of pad 12 positioned opposite eyelet 18 can be bonded to a patient's tooth, such that eyelet 18 extends outward from a patient's tooth. Posts 30 on second side 28 of pad 12 can help provide a larger overall surface area for a bonding agent to adhere, thereby helping increase the integrity of the bond between bracket 10 and the patient's tooth. As shown in FIG. 4, the posts 30 can be oriented in a grid pattern to help provide a consistent and uniform bond to the patient's tooth.

Figure 9:
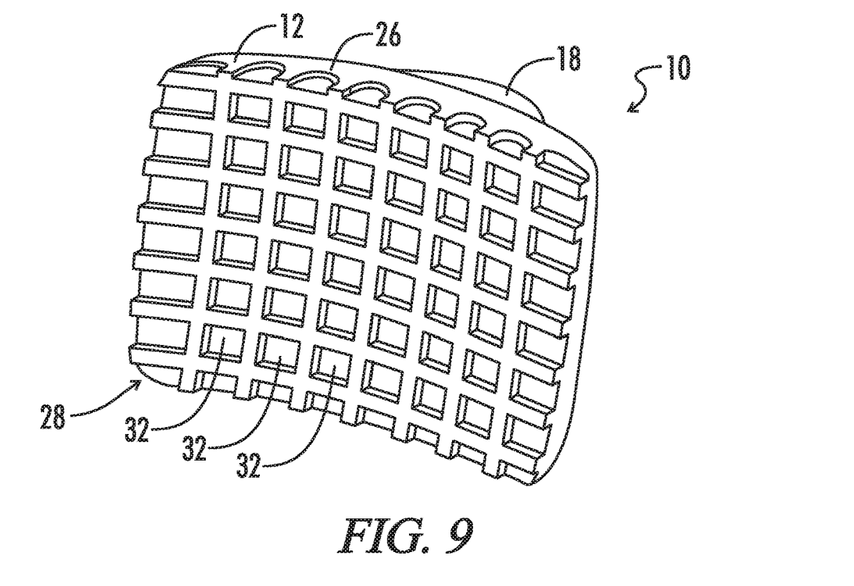
FIG. 9 is a bottom perspective view of another embodiment of an orthodontic bracket wherein the pad includes a plurality of recesses position on the pad opposite the eyelet.

In other embodiments, as shown in FIG. 9, second side 28 of pad 12 can include a plurality of recesses 32 which can help provide the textured surface second side 28 of pad 12. In some embodiments, recesses 32 can be oriented in a grid pattern to help provide a consistent bond characteristic between pad 12 and the patient's tooth. There can be many suitable ways to increase the surface area of second side 28 of pad 12 to help provide a stronger bond with a patient's tooth. For instance, second side 28 can have a roughened surface, or second side 28 can include a mesh like pattern, etc. Other suitable embodiments will be apparent to one of skill in the art.

In embodiments that include posts extending from second side 28 of pad 12 or recesses defined in second side 28 of pad 12, pad 12 can include a top wall 42 and a bottom wall 44 such that a smooth top edge 46 and a smooth bottom edge 48 are produced, as shown in FIG. 4. Bottom edge 48 can be a gingival edge as bottom edge 48 can face the gums 50 of a patient when bracket 10 is bonded to a primary tooth, as shown in FIG. 8. In some embodiments, gingival edge 48 can be a rounded gingival edge such that gingival edge 48 can contour to the curved shape of the upper edge 52 of a patient's gums 50 at the bottom of a primary tooth 54. While FIG. 8 shows bracket 10 attached to primary tooth 54 on the lower teeth of a patient, one of skill in the art will recognize that bracket 10 can be rotated 180 degrees such that bottom or gingival edge 48 faces upward such that bracket 10 can be bonded to a primary tooth on a patient's upper teeth. In other embodiments, all outer edges of pad 12 can be slightly rounded to help avoid any sharp edges of the pad scratching or tearing a patient's gums, lips or cheeks. In still other embodiments, the corners of pad 12 can be rounded to avoid similar damage to the inside of a patient's mouth.

In some embodiments, eyelet 18 and pad 12 can be integrally formed together, as shown in FIG. 1. In other embodiments, eyelet 18 can be mechanically attached to pad 12. Eyelet 18 is shown in FIG. 1 as having a round outer shape. In other embodiments, eyelet 18 can be any suitable shape, including but not limited to, rectangular, triangular, trapezoidal, etc. Pad 12 in some embodiments can have a generally trapezoidal shape as shown in FIGS. 1 and 4, where top and bottom edges 46 and 48 are different sizes. In other embodiments, pad 12 can be any suitable shape, including but not limited to, rectangular, elliptical, hexagonal, etc.

Typically arch wires 24 for orthodontic braces, and particular for passive self-ligating systems, can have a rectangular cross section, as seen in FIG. 2. Generally speaking, the largest arch wire currently in use is a rectangular arch wire having a cross section that is 0.021 inches by 0.025 inches in size. In conventional orthodontic brackets, including passive self-ligating brackets, the channels which receive an arch wire are typically square, rectangular, or rounded. Some channels can be described as being edgewise, or channels that have flat sidewalls that meet to form edges or corners in the channel. As such, particularly in square, rectangular, and edgewise channels, even if the bracket can slide along a rectangular arch wire, if the rectangular arch wire were to be urged to rotate within the channel during the orthodontic treatment, the corners or edges of the arch wire would engage the side walls of a square, rectangular, or edgewise channel. The arch wire can produce forces on the channels of the bracket and thereby produce a torque force or torque vector on the teeth. In applications where brackets are placed on primary teeth, such torque forces applied to primary teeth can cause the primary teeth to twist and torque which can cause the primary teeth to prematurely loosen and fall out, which is undesirable.

To help combat this problem, aperture 20 can be sized to slidingly receive an arch wire 24 of any shape and size, whether round, square or rectangular. In some embodiments, aperture 20 can also be sized to allow arch wire 24 to rotate through at least 90 degrees of rotation to help reduce torque forces on a primary tooth to which orthodontic bracket 10 can be attached as the arch wire expands. In some embodiments, aperture 20 can be sized to allow arch wire 24 to rotate freely within aperture 20 in order to help reduce torque forces on a primary tooth to which orthodontic bracket 10 can be attached. Being able to rotate freely can signify that once arch wire 24 is placed in aperture 20, arch wire 24 can undergo a 360 degree rotation within aperture 20 if necessary, even though arch wire 24 may not actually undergo a full 360 degree rotation during the orthodontic treatment. In some embodiments, aperture 20 can be sized large enough to allow for any arch wire 24 to rotate freely, including the largest rectangular arch wire in use described previously. In some embodiments, aperture 20 can have a round shape, as shown in FIG. 2. Aperture 20 can be dimensioned such that a diameter 34 of aperture 20 can be larger than a diagonal 36 of arch wire 24, such that rectangular arch wire 24 can rotate freely within round or circular aperture 20. The size of an arch wire 24 can be varied according to the needs of the patient, and as such, the size of aperture 20 can be varied to correspond to a particular arch wire 24 size to maintain the freedom of arch wire 24 within aperture 20 to slide and rotate.

Figure 3:
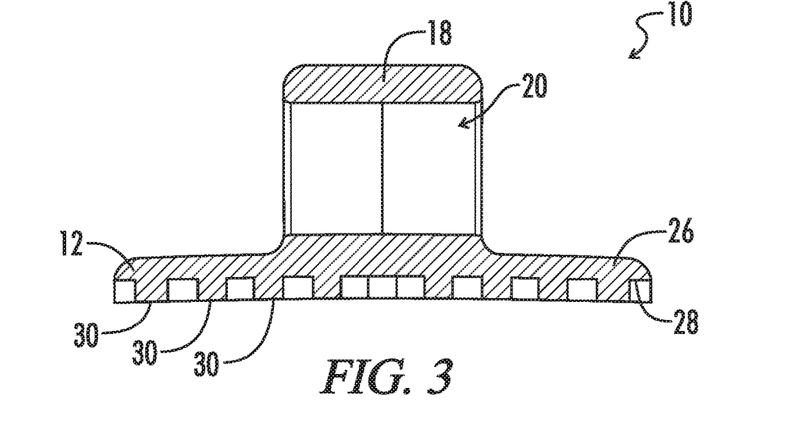
FIG. 3 is a cross section view of the orthodontic bracket of FIG. 1
Figure 5:
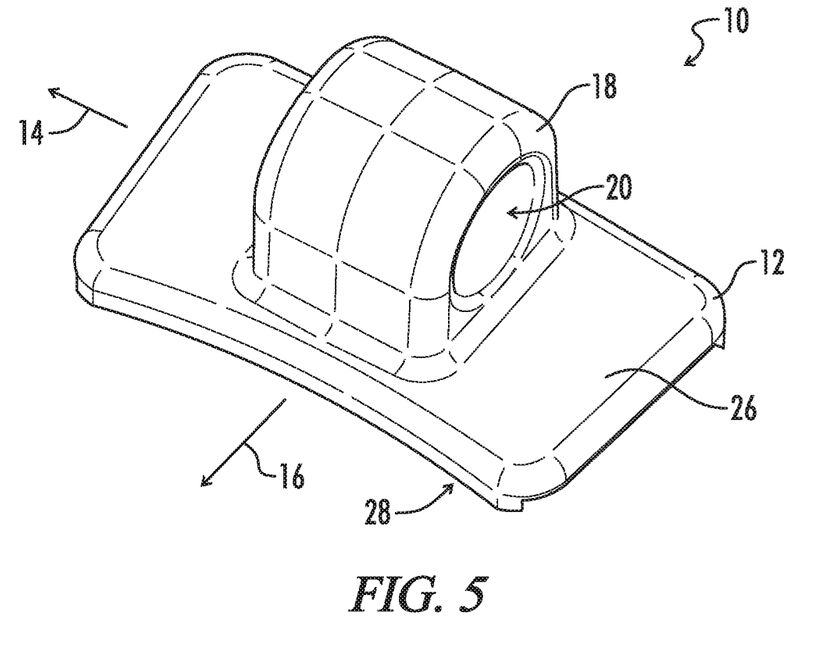
FIG. 5 is a perspective view of another embodiment of an orthodontic bracket of the present disclosure having a curved pad.
Figure 6:
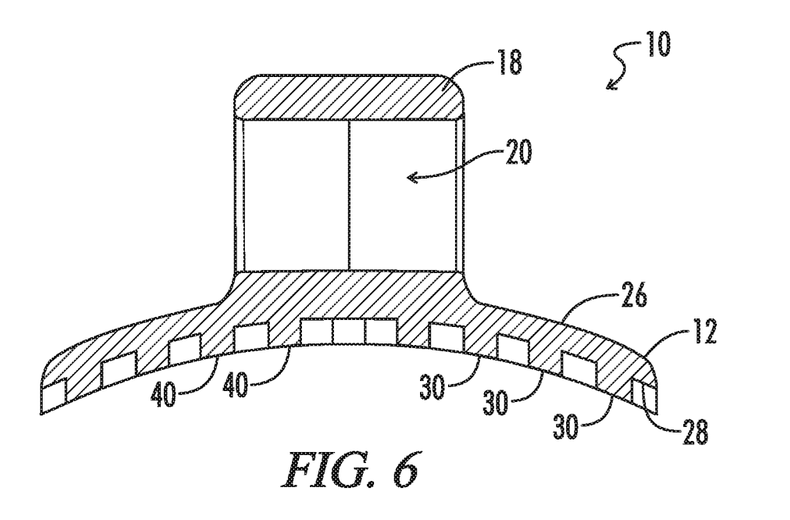
FIG. 6 is a cross section view of the bracket of FIG. 5.

In some embodiments, as shown in FIG. 3, pad 12 can be substantially flat, both in longitudinal direction 14 and lateral direction 16. A flat pad 12 can be positioned on and contour a primary tooth having a substantially flat facial surface, such as a premolar or an incisor tooth. In other embodiments, as shown in FIGS. 5 and 6, pad 12 can be arcuate, pad 12 curving or extending arcuately as it extends in longitudinal direction 14. An arcuate pad 12 can be positioned on and contour a primary tooth 54 with a curved facial surface 38, such as a canine or bicuspid tooth as shown in FIG. 8. Referring again to FIGS. 5 and 6, in some embodiments, the entire pad 12, including first side 26 and second side 28 can be arcuate. In other embodiments, second side 28 can be arcuate or have a concave shape while first side 26 remains substantially flat. In some embodiments including posts 30 extending from second side 28 of pad 12, each post 30 can include a post face 40 which can be curved to correspond to the curvature of pad 12.

In some embodiments, as shown in FIG. 8, pad 12 can be sized such that when pad 12 is bonded to a primary tooth 54, a gap 56 can be formed between gingival edge 48 of pad 12 and the patient's gums 50. Gap 56 can help prevent tartar buildup near the patient's gum line 52 as the area below bracket 10 can be more easily cleaned. Gap 56 can also help prevent discomfort of pad 12 being bonded directly against the gum line 52 of a patient.

Figure 7:
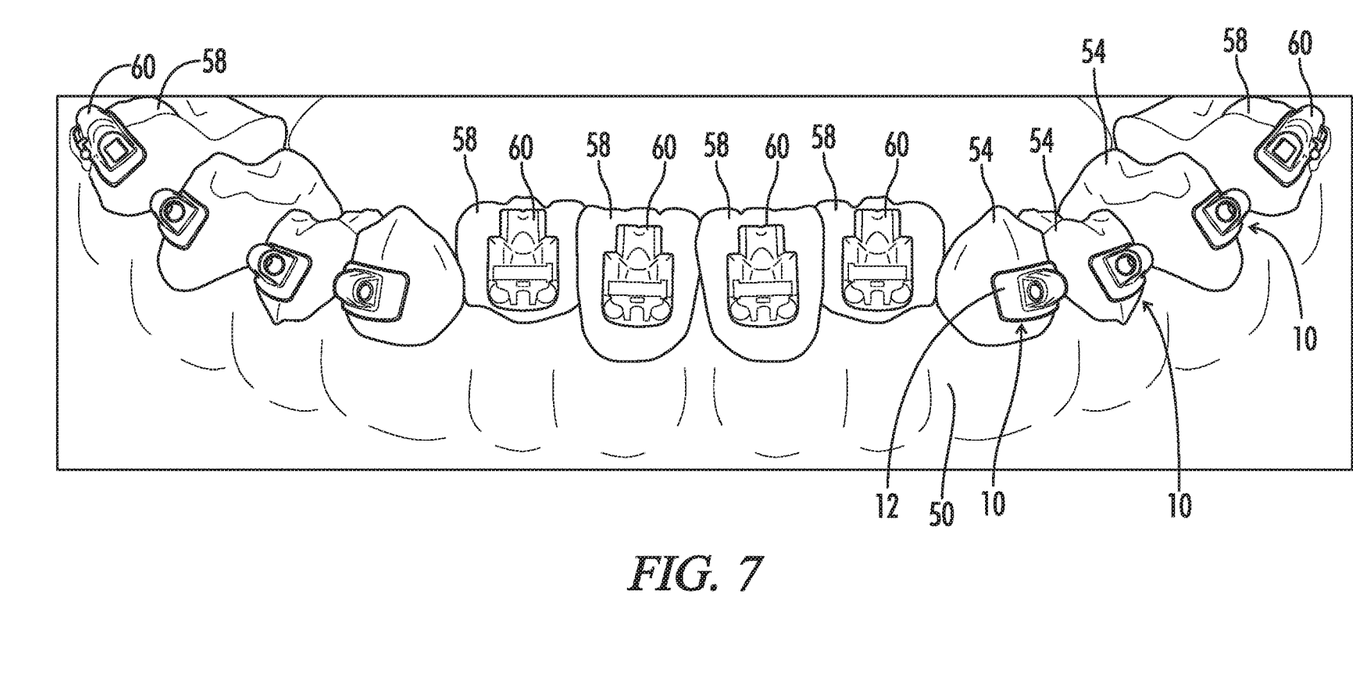
FIG. 7 is a perspective view of the lower teeth of a patient with both primary and permanent teeth and the brackets of FIGS. 1 and 5 on the primary teeth.

Passive self-ligating brackets 60 shown in FIG. 7 are designed for permanent teeth 58 which have much larger facial surfaces than primary teeth 54. As such, passive self-ligating brackets 60 if applied to primary teeth 54 would encroach on the gum line 52 of a patient, which can cause discomfort. Additionally, traditional passive self-ligating brackets 60 have rectangular channels or apertures which correspond closely to the dimensions of a rectangular arch wire which can run through passive self-ligating brackets 60. As such, if passive self-ligating brackets 60 were to be placed on primary teeth 54, passive self-ligating brackets 60 would place substantial torque forces on primary teeth 54 as an arch wire moves and twists during the orthodontic treatment, which could cause premature loosening of primary teeth 54.

Brackets 10 having apertures 20 that are sized to allow arch wires of all shapes and sizes to slide within bracket 10 and rotate freely, which can help reduce the torque forces applied on primary teeth 54. As such, primary teeth 54 can fall out naturally as opposed to falling out because of the orthodontic treatment. Additionally, pad 12 of bracket 10 being sized to fit on facial surface 38 of primary teeth 54 can allow bracket 10 to be bonded to the front of a patient's teeth such that the tongue space in the patient's mouth is not encroached. As such, bracket 10 can help reduce the problems with traditional lingual expansion appliances, including difficulty with speech.

Bracket 10 can act as a guide and support for an arch wire passing from a patient's front permanent teeth to a patient's back permanent teeth. As such, an arch wire does not have to travel a large distance from the front teeth to the back teeth without an interceding support. This can be beneficial, for instance, if a patient were to bite down on a hard food item, which could potentially bend or break the arch wire. Bracket 10 could provide support to the arch wire to help prevent such damage. Having brackets 10 on primary teeth 54 can thus add a significant advantage over the 2×4 method currently being used in Phase 1 or mixed dentition treatment where the primary teeth are bypassed altogether. Having a broken or bent arch wire is generally undesirable, can adversely affect the orthodontic treatment, and often requires emergency appointments to fix the damaged arch wire.

Another problem with the use of traditional or passive self-ligating brackets 60 on primary teeth is that because the pads of traditional brackets can be generally larger than pad 12 of the present disclosure, more bonding agent is required to bond the larger pads to the primary teeth. As such, a substantial force would be required to subsequently remove the larger traditional or passive self-ligating brackets from the primary teeth, if necessary. The increased removal force can have the adverse effect of prematurely pulling out the primary teeth when the brackets are being removed. One advantage of pad 12 of the present disclosure is that pad 12 is sized to fit on a primary tooth 54 and is generally smaller than the pads of traditional or passive self-ligating brackets 60. As such, the amount of bonding agent required to bond pad 12 to the primary tooth can be reduced, and as such the force required to remove pad 12 and bracket 10 from primary tooth 54 can be reduced, which helps reduce the risk of pulling out primary teeth 54 upon removal of bracket 10.

Another advantage of bracket 10 of the present disclosure is the cost of manufacturing, which can be less than the cost to manufacturer more complex passive self-ligating brackets 60. Because primary teeth frequently fall out within a matter of months, an expensive bracket bonded to a primary tooth 54 may simply be thrown away with the tooth, thereby wasting an expensive bracket. Bracket 10 of the present invention can have a potentially lower manufacturing cost, which can help reduce the cost of the orthodontic treatment for Phase 1 or mixed dentition patients by helping reduce unnecessary waste in the treatment.

Bracket 10 can be made out of any suitable material for orthodontic applications, including but not limited to, metals such as stainless steel, gold, titanium, nickel, etc., plastics, ceramics, or any combination thereof. Brackets 10 can be manufactured using any suitable manufacturing method, including but not limited to, machining, injection molding, casting, forming, etc.

As shown in FIG. 1 and FIG. 7-8, another aspect of the present disclosure is a method of attaching orthodontic brackets to orthodontic patients having both primary teeth 54 and permanent teeth 58, the method including the steps of (1) providing an orthodontic bracket 10 having a pad 12 which extends a first distance 13 generally in a longitudinal direction 14 and a second distance 15 generally in a lateral direction 16, first distance 13 being greater than second distance 15, and an eyelet 18 extending from pad 12, eyelet 18 including a round aperture 20 having a central axis 22 oriented transverse to lateral direction 16; and (2) bonding pad 12 of orthodontic bracket 10 to one of primary teeth 54.

In some embodiments, primary teeth 54 can extend from a patient's gums 50, and the bonding step of the method can include orienting pad 12 such that a gap 56 is formed between pad 12 and gums 50 and gum line 52 of the patient when bracket 10 is ponded to primary tooth 54. In some embodiments, primary teeth 54 can include a canine tooth 62, and bracket 10 can be bonded to canine tooth 62. In some embodiments, primary teeth 54 can include a bicuspid tooth 64, and bracket 10 can be bonded to bicuspid tooth 64. In some embodiments, primary teeth 54 can also include an incisor tooth or a premolar tooth, and bracket 10 can be bonded to the incisor tooth or the premolar tooth.

In some embodiments, bracket 10 can be bonded to primary teeth 54 such that longitudinal direction 14 is generally horizontal and lateral direction 16 is generally vertical. As such, pad 12 which extends a greater distance in longitudinal direction 14 can contour or correspond to the generally shorter and wider facial surface 38 of a primary tooth 54. In some embodiments, each of the primary teeth 54 can include a facial surface, and pad 12 can be sized to fit within a facial surface 38 of one of primary teeth 54, and bracket 10 can be bonded to primary tooth 54 such that pad 12 is positioned within or retained entirely within facial surface 38 of one of primary teeth 54. As such, the entire surface area of pad 12 can be utilized to bond directly with a facial surface 38 of a primary tooth 54.

In still other embodiments, the method can further include providing a plurality of orthodontic brackets 10, each orthodontic bracket having a corresponding pad 12 extending a corresponding first distance 13 generally in a corresponding longitudinal direction 14 and a corresponding second distance 15 generally in a corresponding lateral direction 16, corresponding first distance 13 being greater than corresponding second distance 15, and a corresponding eyelet 18 extending from corresponding pad 12, corresponding eyelet 18 including a corresponding round aperture 20 having a corresponding central axis 22 oriented transverse to corresponding lateral direction 16, and bonding corresponding pad 12 of each orthodontic bracket 10 of the plurality of orthodontic brackets to a corresponding primary tooth 54. In some embodiments, a corresponding orthodontic bracket 10 of the present disclosure can be bonded to each of a patient's primary teeth to provide the benefits described above.

Additionally, traditional or passive self-ligating brackets 60 can be bonded to permanent teeth 58. An arch wire can then be passed through each of the passive self-ligating brackets 60 and orthodontic brackets 10. Apertures 20 in orthodontic brackets 10 can be sized such that the arch wire can freely slide and rotate within aperture 20. As such, as the arch wire expands outward, the arch wire can be supported by brackets 10 while torque forces on primary teeth 54 can be minimized.

Thus, although there have been described particular embodiments of the present invention of a new and useful Orthodontic Bracket For Primary Teeth, it is not intended that such references be construed as limitations upon the scope of this invention.

What is claimed is:

1. An orthodontic bracket system for receiving an arch wire of an orthodontic patient having both primary teeth and permanent teeth, the bracket system comprising:
   a plurality of primary tooth orthodontic brackets for placement on the patient's primary teeth, each primary tooth orthodontic bracket including:
      a pad sized to fit on and be contained within one of the primary teeth, the pad extending a first distance generally in a longitudinal direction and a second distance generally in a lateral direction, the first distance being greater than the second distance, the ratio between the first distance and the second distance being greater than about 1.5;
      an eyelet extending from the pad; and
      a round aperture defined through the eyelet, the round aperture having a central axis oriented transverse to the lateral direction;
      wherein the aperture is sized to slidingly receive the arch wire and allow free rotation of the arch wire within the aperture; and
   a plurality of self-ligating brackets for placement on the patient's permanent teeth, each self-ligating bracket including:
      a self-ligating bracket pad sized to fit on and be contained within one of the permanent teeth, the self-ligating bracket extending a third distance in a longitudinal direction and a fourth distance in a lateral direction, the fourth distance being greater than or equal to the third distance; and
      a channel for receiving the arch wire, the channel oriented transverse to the lateral direction.

2. The bracket system of the claim 1, wherein each pad is arcuate along the longitudinal direction.

3. An orthodontic treatment method for an orthodontic patient having both primary teeth and permanent teeth, the method comprising the steps of:
   (a) providing an orthodontic bracket having:
      a pad extending a first distance generally in a longitudinal direction and a second distance generally in a lateral direction, the first distance being greater than the second distance; and
      an eyelet extending from the pad, the eyelet including a round aperture having a central axis oriented transverse to the lateral direction; and
   (b) bonding the pad of the orthodontic bracket to one of the patient's primary teeth.

4. The method of claim 3, wherein the patient's primary teeth extend from a patient's gums, and step (b) of the method further comprises orienting the pad on one of the patient's primary teeth such that a gap is formed between the pad and the patient's gums.

5. The method of claim 3, wherein:
   each of the patient's primary teeth has a facial surface; and
   the pad is sized to be contained within the facial surface of one of the patient's primary teeth when the pad is bonded to the primary tooth.

6. The method of claim 3, wherein when the pad is bonded to one of the patient's primary teeth, the pad is oriented such that the central axis of the aperture is generally horizontal on the patient's primary tooth.

\* \* \* \* \*